(12) United States Patent
Cambray Roma et al.

(10) Patent No.: US 12,288,610 B2
(45) Date of Patent: Apr. 29, 2025

(54) SYSTEM AND METHOD FOR PROCESSING MEDICAL IMAGES

(71) Applicant: Optellum Limited, Oxford (GB)

(72) Inventors: Aleix Cambray Roma, Oxford (GB); Carlos Federico Arteta Montilva, Oxford (GB)

(*) Notice: Subject to any disclaimer, the term of this patent is extended or adjusted under 35 U.S.C. 154(b) by 325 days.

(21) Appl. No.: 17/557,471

(22) Filed: Dec. 21, 2021

(65) Prior Publication Data

US 2023/0197248 A1  Jun. 22, 2023

(51) Int. Cl.
| | |
|---|---|
| G06Q 10/00 | (2023.01) |
| G06T 7/00 | (2017.01) |
| G16H 30/40 | (2018.01) |
| G16H 50/20 | (2018.01) |
| G16H 50/30 | (2018.01) |

(52) U.S. Cl.
CPC ........... *G16H 30/40* (2018.01); *G06T 7/0012* (2013.01); *G16H 50/20* (2018.01); *G16H 50/30* (2018.01); *G06T 2207/20081* (2013.01); *G06T 2207/30004* (2013.01); *G06T 2207/30168* (2013.01)

(58) Field of Classification Search
CPC ......... G16H 30/40; G16H 50/30; G16H 50/20
See application file for complete search history.

(56) References Cited

U.S. PATENT DOCUMENTS

| | | | | |
|---|---|---|---|---|
| 7,490,085 B2* | 2/2009 | Walker | ................... | G16H 50/70 600/125 |
| 9,589,374 B1 | 3/2017 | Gao et al. | | |
| 11,195,624 B2* | 12/2021 | Holmes | ................... | G16H 50/80 |
| 2018/0336484 A1* | 11/2018 | Hunt | ................... | G06N 7/01 |
| 2020/0279369 A1 | 9/2020 | Kadir et al. | | |
| 2020/0402644 A1 | 12/2020 | Zhou et al. | | |
| 2021/0150703 A1 | 5/2021 | Levanony et al. | | |
| 2021/0287795 A1 | 9/2021 | Declerck et al. | | |
| 2022/0012877 A1* | 1/2022 | Buckler | ................ | G06T 7/0012 |
| 2022/0130520 A1* | 4/2022 | Xia | ................ | G06T 7/0014 |

OTHER PUBLICATIONS

Janne J Nappi et al: "Application of CT Acquisition Parameters as Features in Computer-Aided Detection for CT Colonography", Oct. 1, 2012 (Oct. 1, 2012), Abdominal Imaging. Computational and Clinical Applications, Springer Berlin Heidelberg, Berlin, Heidelberg, pp. 69-77, XP047015865, ISBN: 978-3-642-33611-9.
EPO Article 94(3) Communication; EPO Application Serial No. 22 213 238.3-1122; Dec. 23, 2024; pp. 1-6.

* cited by examiner

*Primary Examiner* — Rajesh Khattar
(74) *Attorney, Agent, or Firm* — Optimus Patents US, LLC

(57) ABSTRACT

A CADx system and method for analysing medical images to determine a disease risk score is described. The system comprising: an input circuit for receiving an input comprising at least one medical image; a dynamic protocol adaptation circuit comprising a protocol adaptation circuit for receiving and analysing scan protocol information and providing an output from the protocol adaptation circuit as an input or modification to a disease prediction model based on the received scan protocol information; and an output circuit to produce an output that is a disease risk score calculated from the disease prediction model for the at least one medical image.

14 Claims, 9 Drawing Sheets

Embodiment 2: Protocol-based Adaptation Module $G$ that parametrizes DPM model $F$

SYSTEM AND METHOD FOR PROCESSING MEDICAL IMAGES

FIELD OF INVENTION

This invention relates to the field of Computer Aided Diagnosis (CADx) systems and methods for assisting the interpretation of medical scan images to support clinicians in healthcare. In particular, the field relates to risk Computer Aided Diagnosis systems to assist the reading and reporting of medical scan images by radiologists and the interpretation of the radiologist's report by the physician responsible for patient care.

BACKGROUND OF INVENTION

In the field of medical imaging, a variety of technologies can be used to investigate biological processes and anatomy. The following examples are types of scan that may be used to provide medical images: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an "imaging modality".

Typically, a scan provides a "dataset". The dataset comprises digital information about the value of a variable at each of a plurality of spatial locations in either a two-dimensional or (more typically) a three-dimensional space. As a specific example, a CT scan may provide images of the chest of a patient. Such a CT scan might, as a more specific example, show lung nodules in the chest.

Computer Aided Detection (CADe) devices serve to assist its users (e.g. typically clinicians) in assessing the medical images. CADe devices need to provide a clinician with standardised, objective and repeatable information. The information typically relates to particular anatomical regions, including both normal tissue and lesions, within a person. CADe devices may be used as a so-called 'Second Reader' system. Second Reader Systems are based on an approach whereby a radiologist first looks at an image resulting from a scan, for example a mammogram. The radiologist will then, based on training and experience, identify areas of the scan where the radiologist considers that there may need to be a further investigation, for example a biopsy. However, the radiologist can then consider the CADe findings. Those findings might involve a display to highlight any additional suspicious regions on the mammogram. The radiologist will then, based on training and experience, look at those further areas of the scan. The CADe device is thereby performing a second look at the scan. The results of the second look at the scan may be that the radiologist will be directed to areas of the scan that he/she had overlooked. In this way, CADe devices are designed to reduce 'false negatives', which are also termed 'missed findings'. Thus, CADe devices perform a support role to clinicians.

Computer Aided Diagnosis (CADx) devices are a related technology to CADe. CADx devices attempt to solve a different problem and relate generally to risk assessment. Instead of focusing on potentially missed findings as in CADe, they try to assist the user to classify findings correctly, either as malignant or benign in the case of potentially cancerous lesions. They rely on the user to identify abnormalities, but then typically provide a score that is indicative of the risk of malignancy. There are many examples of such CADx devices proposed within the academic literature. However, few systems are available commercially, and hence used in clinical practice. This discrepancy is indicative of the difficulties in deploying practical systems with the known approaches. The output of known CADx devices is typically some kind of score. That score indicates the risk or likelihood of disease, or its absence. An example of a commercial CADx device is the 'Transpara™' product from 'Screenpoint™'. There are many non-clinical CADx devices in the academic literature.

State-of-the-art CADx devices are built around machine learning models. These models are generic algorithms with "learnable" parameters which are fitted using training data such that the model can be used to make predictions on previously unseen data. For example, a machine learning model built to predict whether a lung nodule on a CT image is malignant, can be fitted to a collection of datasets of CT images of malignant and benign lung nodules. Such a model could then be suited to assist a clinician in estimating the risk that a lung nodule they found in their practice could be malignant. The process of fitting the model parameters to the training data is referred to as the model training, while the process of using the model to make a prediction on input data is referred to as inference. The output of the inference in the case of a machine learning-based CADx device would typically be a score indicative of the likelihood that the input sample contains the disease of interest, for instance a score for malignancy in the case of the lung nodules.

The visual information contained in the scans which a CADx device operates on is the result of the physical space studied (i.e. what anatomy is scanned), the medical imaging modality (e.g., CT, MM, etc) and the set of parameters which are chosen to acquire and process the final image. The latter can be referred to as the scan protocol parameters and can be broadly divided into acquisition parameters and reconstruction parameters. Acquisition parameters are generally those which are fixed or determined at the time of the scan (e.g. scan contrasting agent, tube voltage for the image acquisition, tube current for the image acquisition, scanning mode, field of view, slice spacing). Reconstruction parameters are those which are chosen at the time of processing the acquired raw signal in order to obtain a final image (e.g., reconstruction algorithm, convolutional kernel, slice thickness, reconstruction field of view). The choice of protocol is done by the clinician depending on, for example, the reason for the scan, the part of the body scanned and the patient's characteristics. The combination of these parameters can have a marked effect on the resulting image, affecting spatial resolution, slice spacing, sharpness, and noise level, amongst other things.

Depending on the context in which a CADx device operates, different levels of variability between scan protocol parameters can be expected, and hence variability in image appearance. When screening for a specific condition such as lung cancer, variations in acquisition and reconstruction protocol may be minimal, but for CADx devices which are meant to operate on incidental findings, the opposite is true. As an example, when a lung nodule is first detected incidentally on a CT scan, the scan protocol of the medical image in which it is found would have been optimized for the reason the scan was done, for example, for cardiac assessment. Follow-up scans could then be taken changing the acquisition and reconstruction protocol to better suit lung nodule assessment, introducing further variability with respect the initial scan. Likewise, after a nodule is first detected and characterized (e.g., in size and morphology), the protocol of follow-up scans may be changed to better suit the assessment of those morphological characteristics. For instance, if a nodule is seen to be spiculated i.e., a presentation of radially arranged sharp branches spawning from the nodule boundary, harder reconstruction kernels may be chosen from that point onwards to provide finer detail. Reconstruction kernels are filters applied to the raw data from a CT scan prior to reconstructing the final image, which modify its frequency contents. The choice of the reconstruction kernel typically involves a trade-off between detail and noise in the final image. Using harder kernels will result in sharp detailed images with unwanted noise while softer kernels will result in blurrier images with less noise. Another common source of image variability is the usage of contrast agents, which are typically used to enhance the contrast between anatomical structures that would otherwise have been indiscernible, such as the internal structure of the liver, or to highlight structures with high vasculature. A clinician could therefore choose to use a contrast agent in order to highlight vasculature around a suspicious lesion, such as a lung nodule. Therefore, in the scenario of incidentally detected lung nodules, important variability in scan and protocol parameters can be expected between patients, and even between follow-up images of the same patient.

In the context of machine learning-based CADx devices, the visual variations arising from different scan protocols can lead to different inner representations obtained by the model and in turn influence the prediction ability of the CADx device. An example of this effect would be a CADx device which, when given two scans of the same anatomical structure reconstructed with different parameters, yields two significantly different malignancy scores. Another issue which arises from training CADx systems with different protocols is that performance may not be comparable across protocols, especially on those protocol regimes the CADx system has not been trained extensively in, therefore leading to potential failure modes when clinicians use the CADx device on these types of scans.

Currently, in CADx devices which only take the scan as input, these issues are addressed by collecting large enough training data sets, which contain as varied a distribution of scan protocols as possible in order to hopefully (a) learn a robust protocol-invariant representation (b) generalise performance to all seen protocols. The resulting CADx device then needs to be validated through a series of sub-analyses in order to assess both stability of prediction as well as performance across several different protocol parameters. However, this approach has several disadvantages. Firstly, it requires large amounts of training data for each possible protocol, as the presence of an imbalance generally would result in poor performance for those protocols which have less support in the training dataset. It also requires enough validation data with different protocols, and even more challenging, a substantially large number of scans each with a set of alternative reconstructions to assess stability. Secondly, it relies on the model computing an intermediate common representation through a set of operations that is common for all scan protocols, which in turn may not be optimal for all or some of the scan protocol and may hurt the overall predictive performance of the CADx device.

This invention addresses the scan protocol variability issue by introducing to the CADx device the ability to exploit each scan's protocol information in order to improve its predictive performance. The need for such an approach comes from the fact that different protocols yield visually different representations of the same scan, and therefore there is a need to automatically adapt CADx devices and the specific processing steps they perform on the image depending on the scan protocol parameters.

SUMMARY OF THE INVENTION

Accordingly, the invention seeks to mitigate, alleviate, or eliminate one or more of the above mentioned disadvantages singly or in any combination.

According to the invention there is provided a CADx system for analysing medical images and determining a disease risk score for the image comprising: an input circuit for receiving an input comprising at least one medical image; a dynamic protocol adaptation circuit for receiving and analysing scan protocol information and providing an output from the dynamic protocol adaptation circuit as an input to a disease prediction model based on the received scan protocol information; and an output circuit to produce an output that is a disease risk score calculated from the disease risk model for at least one medical image.

In a preferred embodiment of the invention, the scan protocol information comprises at least one of acquisition parameters, reconstruction parameters and derived protocol features Further preferably, the acquisition parameters comprise one of more of: details of a scan contrast agent; tube voltage for the image acquisition; tube current for the image acquisition; beam filter type; scanning mode; field of view and slice spacing, and the reconstruction parameters comprise one or more of reconstruction algorithm, slice thickness and convolutional kernel.

Preferably, the derived protocol features are features resulting from the combination of reconstruction parameters and/or acquisition parameters and/or the medical image.

In a preferred embodiment of the invention, the derived protocol features can be noise level, spatial resolution and image sharpness and can be derived from the input medical image.

Further preferably, the output of the dynamic protocol adaptation circuit provided as an input to the disease prediction model is either a data input, or an adjustment or modification to the disease prediction model.

In an embodiment of the invention at least one medical image input to the input circuit is also provided to at least one of the dynamic protocol adaptation circuit and the disease prediction model.

Preferably, the input circuit receives multiple input images over a period of time to assess changes in structures show in the images.

Further preferably, the disease prediction model includes one or more static parameters that are independent of the scan protocol for the input image, wherein the adjustment or modification to the disease prediction model resulting from the output of the dynamic protocol adaptation circuit, affects the dynamic parameters in the disease prediction model, while the static parameters remains unchanged.

In an embodiment of the invention the output further comprises a warning that the scan protocol information is inadequate and the disease risk score may not be reliable.

An embodiment of the invention may preferably further comprise a protocol gatekeeper circuit that receives the scan protocol information before it is provided to the dynamic protocol adaptation circuit, and determines if the scan protocol information is inadequate.

In an embodiment of the invention, the input image is one of: a CT image, an MRI image, a PET image, an X-ray image, an ultrasound image or a SPECT image.

Further preferably, the input further comprises one or more of: biomarkers for the patient or clinical parameters for the patient, wherein the biomarkers and clinical parameters comprise at least one of: patient age, patient sex, family and clinical history, results of blood tests, results of lung function tests.

Further preferably, the disease is a lung disease.

In a further embodiment of the invention there is also provided a method for analysing medical images and determining a disease risk score for the image the method comprising the following step: receiving at least one input medical image; analysing scan protocol information with a dynamic protocol adaptation circuit and providing an output from the dynamic protocol adaptation circuit as an input to a disease prediction model based on the analysed scan protocol information; and producing an output that is a disease risk score calculated from the disease prediction model for the at least one medical image.

Preferably, the step of providing an output from the dynamic protocol adaptation circuit as an input to a disease prediction model comprises further comprising the step of: providing the input as either a data input, or an adjustment or modification to the disease prediction model.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Overview of the Invention

In the context of a CADx device that is based on a machine learning model to produce a disease risk score for input medical data, this invention addresses the need to account for the scan acquisition and/or reconstruction protocol when processing input medical data on a disease prediction model. The dependence of the output disease prediction on the scan protocol can be embodied in several ways by, for example, in one embodiment of the invention, treating the scan protocol information as another input to the CADx model, by using scan protocol information to dynamically adapt the CADx model itself or by using the scan protocol information to dynamically adapt the medical input data.

An embodiment of the invention relates to the dynamic protocol adaptation circuit, a circuit which can form part of the CADx device. The dynamic protocol adaptation circuit processes some or all of the information related to the scanning protocol of the input medical image(s) and generates an output which is then used either as an input to the disease prediction model or alternatively to adapt the CADx disease prediction model to that specific scan protocol. The final output from the CADx device is preferably a disease risk score.

Figure 1:
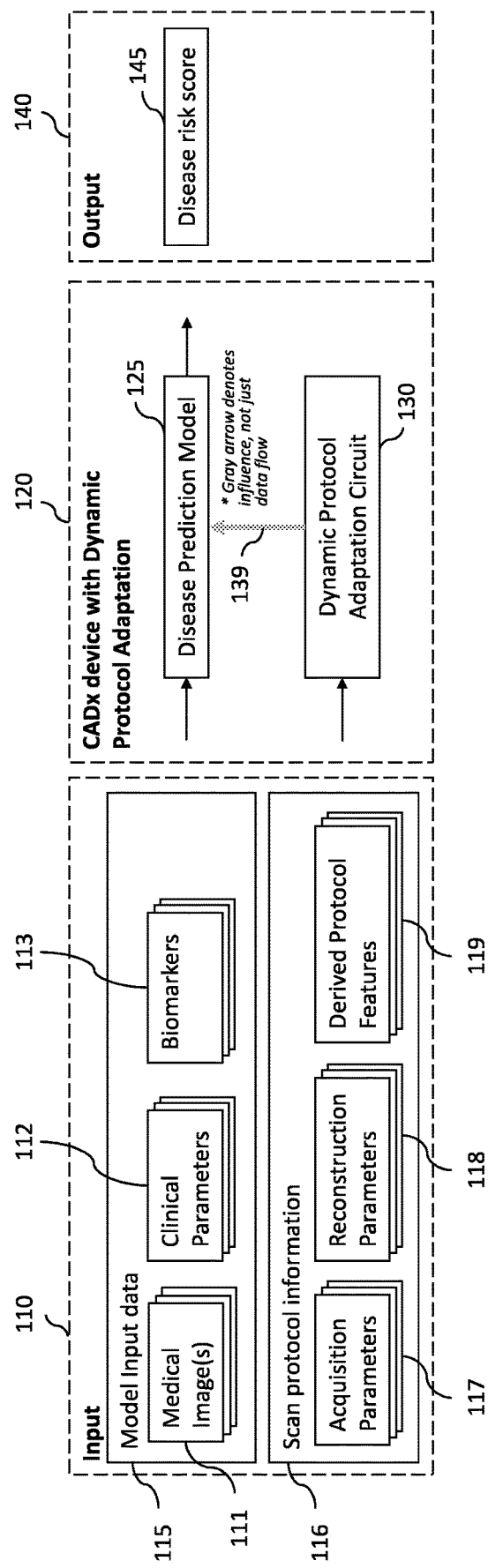
FIG. 1 illustrates a CADx system according to an embodiment of the invention.

In more detail, FIG. 1 illustrates an embodiment of the invention showing a CADx device with dynamic protocol adaptation. That is, the figure shows a machine learning based CADx device (120) with a dynamic protocol adaptation circuit (130). In a preferred embodiment of the invention, the input to the CADx device (120) is a unit of input data (115) containing at least one medical scan image (111), possibly in combination with clinical parameters (112) such as patient age and sex, and the result of relevant tests such as biomarkers (113), e.g., a test for a gene mutation associated with an increased risk of cancer. Other examples of clinical parameters are results of blood tests or lung function tests, patient or family history of disease or other clinical history, body weight, and location of a suspicious lesion. Preferably the at least one medical scan image is one of: a CT image, an MRI image, a PET image, an X-ray image, an ultrasound image or a SPECT image. In an embodiment of the invention the image will include all or part of an image of the patients lungs. Like standard CADx devices, when the input data (115) is presented to the input circuit (110) of the CADx device (120), the data is processed by a machine learning model (125) that is trained to predict a risk score of a disease given the input data. Specifically, the disease prediction model (125) performs a series of mathematical operations on the values of the input data resulting in a disease risk score (145) that is provided via the output circuit (140). Preferably, the disease risk score will be a risk score for a lung disease such as lung cancer. Unlike standard CADx devices, the CADx device with dynamic protocol adaptation (120) in an embodiment of this invention includes a dynamic protocol adaptation circuit (130) for receiving and analysing scan protocol information. The dynamic protocol adaptation circuit (130) is capable of generating a set of output values or parameters which are input to the disease prediction model (125) preferably either as data inputs or as model adjustments. These output values or parameters are generated based on information specific to the scan protocol information (116) of the input medical image(s) (111) provided to the input circuit.

As an example, in the context of a CT scan as provided in an embodiment of the invention, the scan protocol information may be composed of one or more acquisition parameters (117) such as the presence of a scan contrasting agent, the tube voltage for image acquisition, the tube current for image acquisition, beam filter type, scanning mode, field of view and slice spacing; and/or of one of more reconstruction parameters (118) such as the reconstruction algorithm and convolutional kernel. The scan protocol information (116) could also be composed of derived features (119) resulting from the combination of several of the aforementioned protocol acquisition and reconstruction parameters. These could be, but are not restricted to, slice thickness, slice spacing, spatial resolution, noise level and image sharpness. Similar parameters may be used for the scan protocol information when the input scan image is an MRI image, a PET image, an X-ray image, an ultrasound image or a SPECT image The dynamic protocol adaptation circuit (130) is preferably based on a machine learning model and can be trained in conjunction to the disease prediction model (125). In an embodiment of the invention, this is achieved through processing the received scan protocol information (116), and possibly other information that may be available from the input medical scan image itself (111), through a series of mathematical operations to generate changes and/or extra inputs to the disease prediction model (125) which are then applied to each sample of data in the training data set. This set of protocol-informed inputs to the disease prediction model (125) tailor the internal operations on the medical data (115) to each scan's protocol, therefore differentiating this device from current CADx systems which apply the same operations to medical data irrespective of its imaging protocol.

Here, in the context of a general model which transforms input data into an output, an internal representation is any form the data takes after each of the potential operations the model comprises.

In some parts of the following descriptions, the disease prediction model (125) may be shortened to DPM and the dynamic protocol adaptation circuit (130) may be shortened to DPA.

Implementation of the CADx Device with Dynamic Protocol Adaptation

Figure 2A:
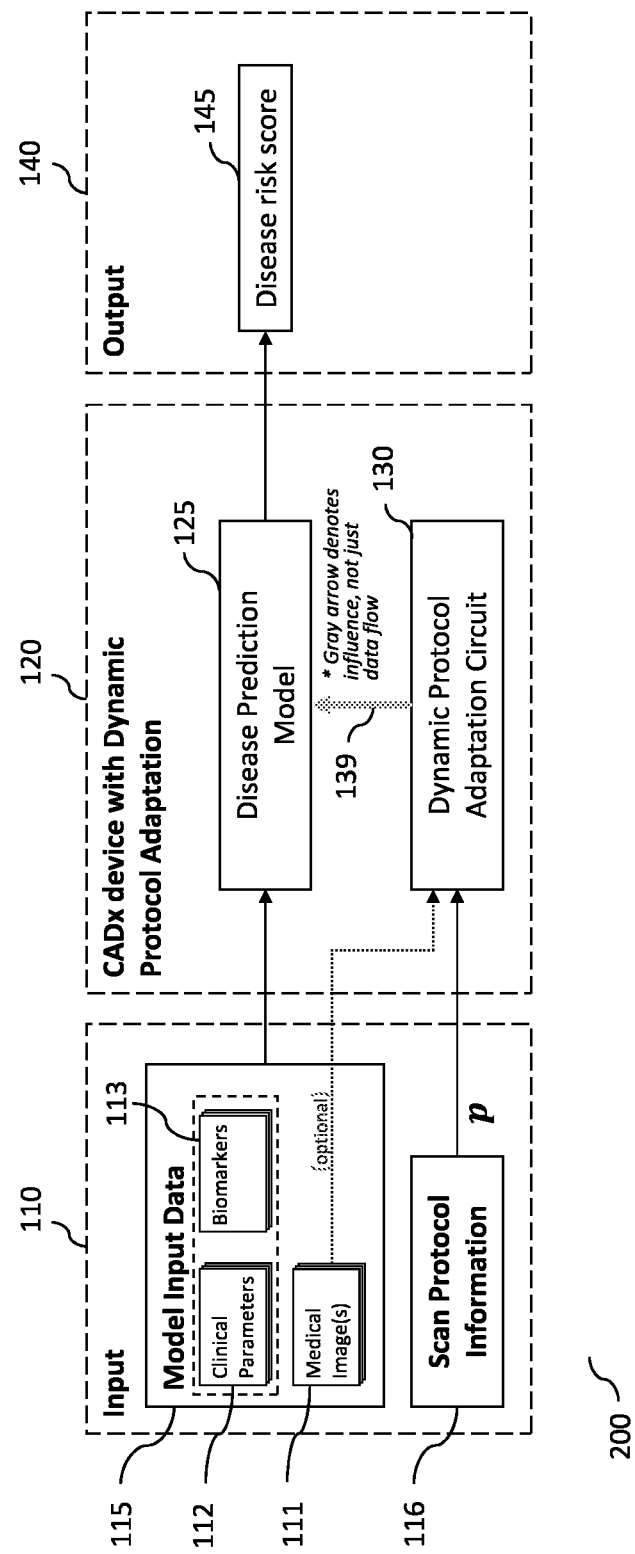
FIG. 2A shows a CADx system according to a first embodiment of the invention.
Figure 2B:
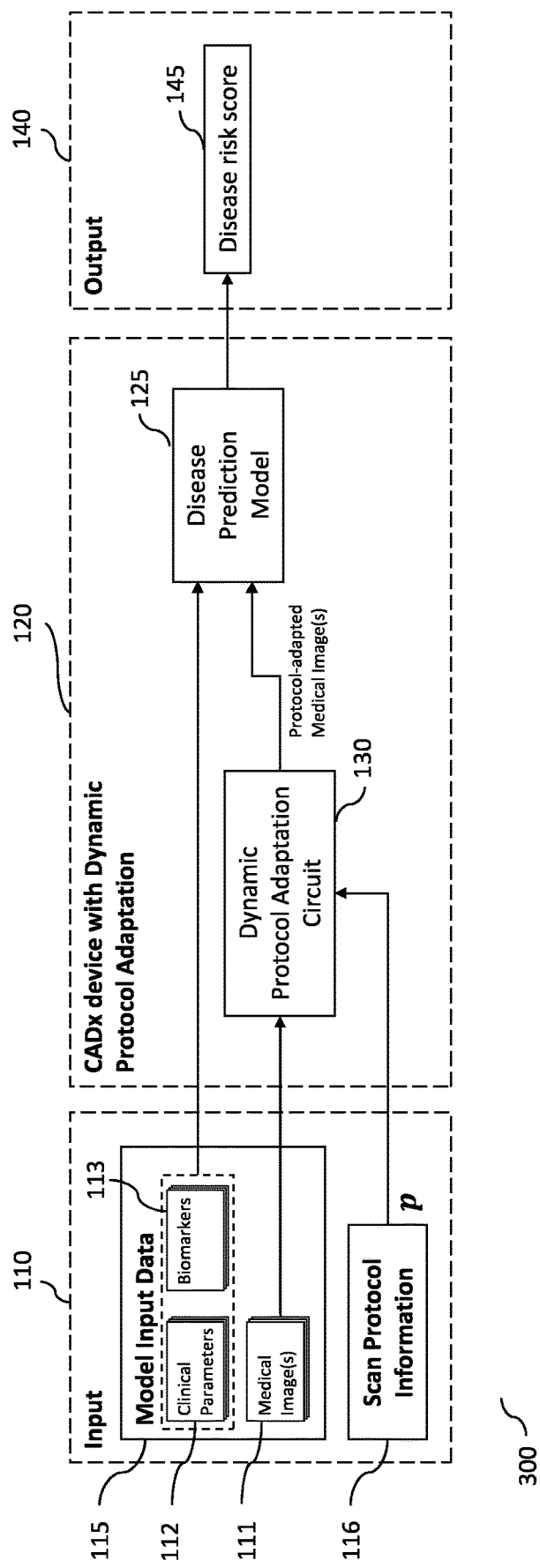
FIG. 2B shows a CADx system according to an alternative embodiment of the invention.

FIG. 2A and FIG. 2B illustrate more detailed arrangements of possible embodiments of this invention.

In some examples of this invention, as illustrated in FIG. 2A, the disease prediction model (125) takes as input all the medical input data (113) received at the input circuit (110) and then incorporates the output of the dynamic protocol adaptation circuit (130) as a set of inputs or adjustments to the disease prediction model. This influence is denoted by the arrow (139) from dynamic protocol adaptation circuit (130) to disease prediction model (125). In these examples, the processing of the medical image(s) (111) by the disease prediction model (125) is conditioned on the scan protocol information (116). Two specific embodiments of the invention which fall under this paradigm are proposed later on:

Embodiment 1—Scan protocol information is used by DPA (130) to generate a representation used as input to DPM (125)

Embodiment 2—Scan protocol information is used by DPA (130) to adjust DPM (125) through parametrisation In some other examples of this invention, as illustrated in FIG. 2B, the disease prediction model (125) does not receive the original medical image(s) (111) directly as input. The dynamic protocol adaptation circuit (130) acts as a protocol-conditioned medical image adapter which takes as input the medical image(s) (111) and the scan protocol information (116), and then generates a protocol-dependent representation of the medical image(s) (111) which are then input to the disease prediction model (125) from the dynamic protocol adaptation circuit (130) alongside the original and optional clinical parameters (112) and biomarkers (113) in the input data (115). One embodiment of the invention is proposed which falls under this paradigm:

Embodiment 3—Scan protocol information is used by DPA to adapt medical image(s) before inputting to DPM Embodiment 1—Scan Protocol Information is Used by DPA to Generate a Representation Used as Input to DPM In some examples of the invention, the approach to scan protocol-based adaptation is embodied through providing the disease prediction model (125) with either the scan protocol information (116) directly or an embedding representation of the scan protocol information (116).

Figure 3A:
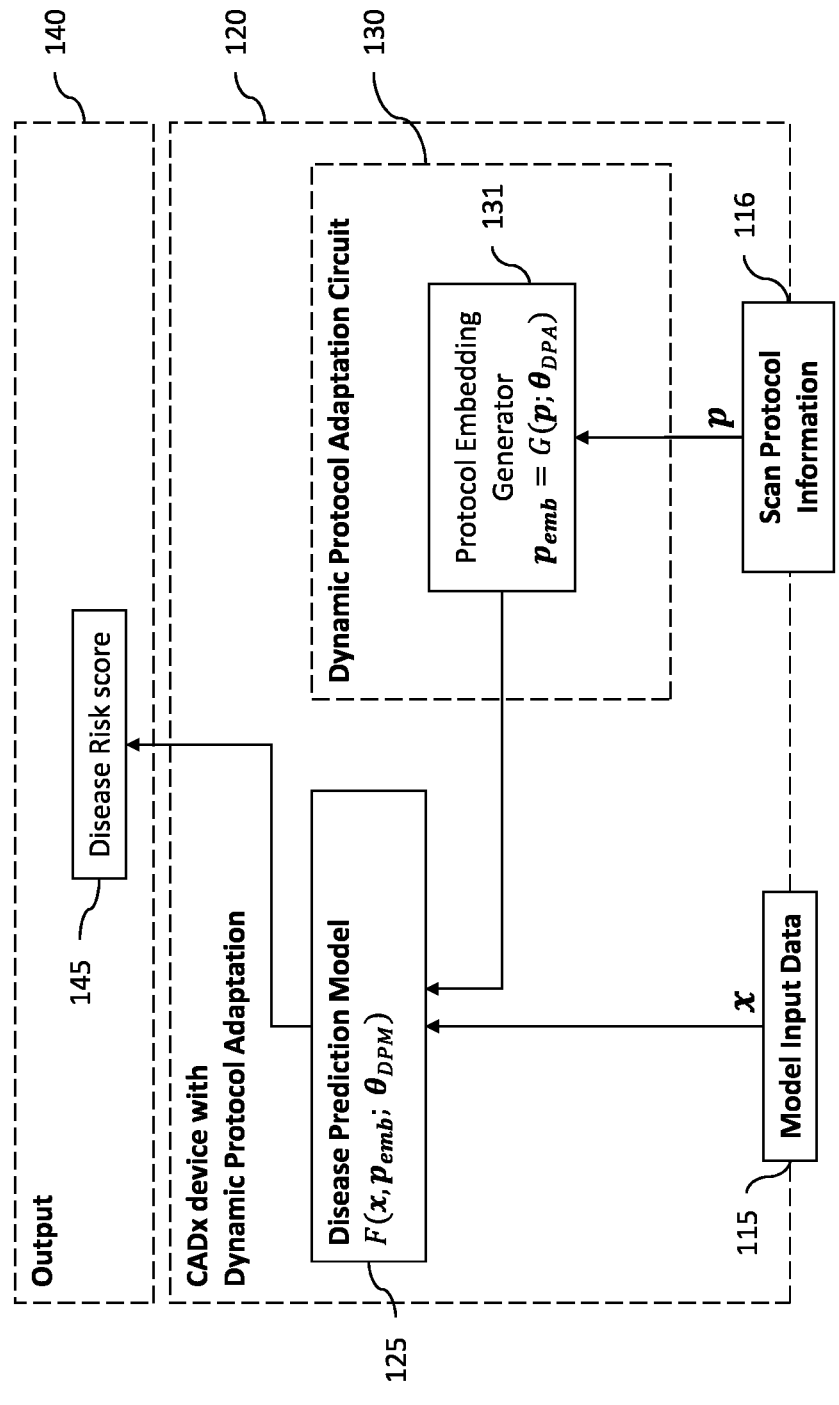
FIG. 3A shows an embodiment of the CADx system with embedded protocol information.

FIG. 3A shows a diagram of an example implementation of such a CADx device (120) with this type of dynamic protocol adaptation circuit (130). Central to the CADx device (120) is a machine learning model for disease prediction (125) that receives medical model input data (115) from the input circuit. The disease prediction model (125) also receives scan protocol information preferably as input in an embedded form, where the protocol parameters are encoded or represented in numerical format, from the dynamic protocol adaptation circuit (130). In this example of the invention, the dynamic protocol adaptation circuit (130) is a circuit which contains a protocol embedding generator (131) which takes the scan protocol information, p, (116) and transforms it into a representation, $p_{emb}$, which in some examples of the invention is a multi-dimensional vector containing scalar values. This vector representation of the scan protocol information is input to the disease prediction model (125). In some examples of this invention, this protocol embedding generator (131) is another machine learning model with parameters $\theta_{DPA}$. Such a machine learning model could be a neural network for example. Then, the protocol embedding generator (131) performs a mapping transformation, G, such that:

$$p_{emb} = G(p; \theta_{DPA}) \quad (1.1)$$

In some other examples of the invention, the protocol embedding generator (131) may not be a machine learning model but a hand-crafted process which transforms raw scan protocol parameters (116) to scan protocol embeddings $p_{emb}$.

The disease prediction model (125) then can be seen as a set of operations to the combination of medical input data, x, (115) and the embedded scan protocol information $p_{emb}$ to produce a disease risk score:

$$\text{DiseaseRiskScore} = F(x, p_{emb}; \theta_{DPM}) \quad (1.2)$$

In this example of the invention, the scan protocol information is transformed alongside and combined with the medical input data (115) in order to condition the output from the output circuit (140), which is the disease risk score (145). Preferably the disease risk score will be for lung disease.

In some examples of the invention, the disease prediction model (125) and the dynamic protocol adaptation circuit (130) can both be part of the same trainable machine learning model as, for example, a pair of combined neural networks and/or convolutional neural networks which can be trained end-to-end. This would allow for simultaneous training of both the disease prediction model (125) and the dynamic protocol adaptation circuit (130). In this context, training means to find the values of the parameters of a machine learning model which minimise a particular error metric over a training set of data through computational optimisation.

Figure 4A:
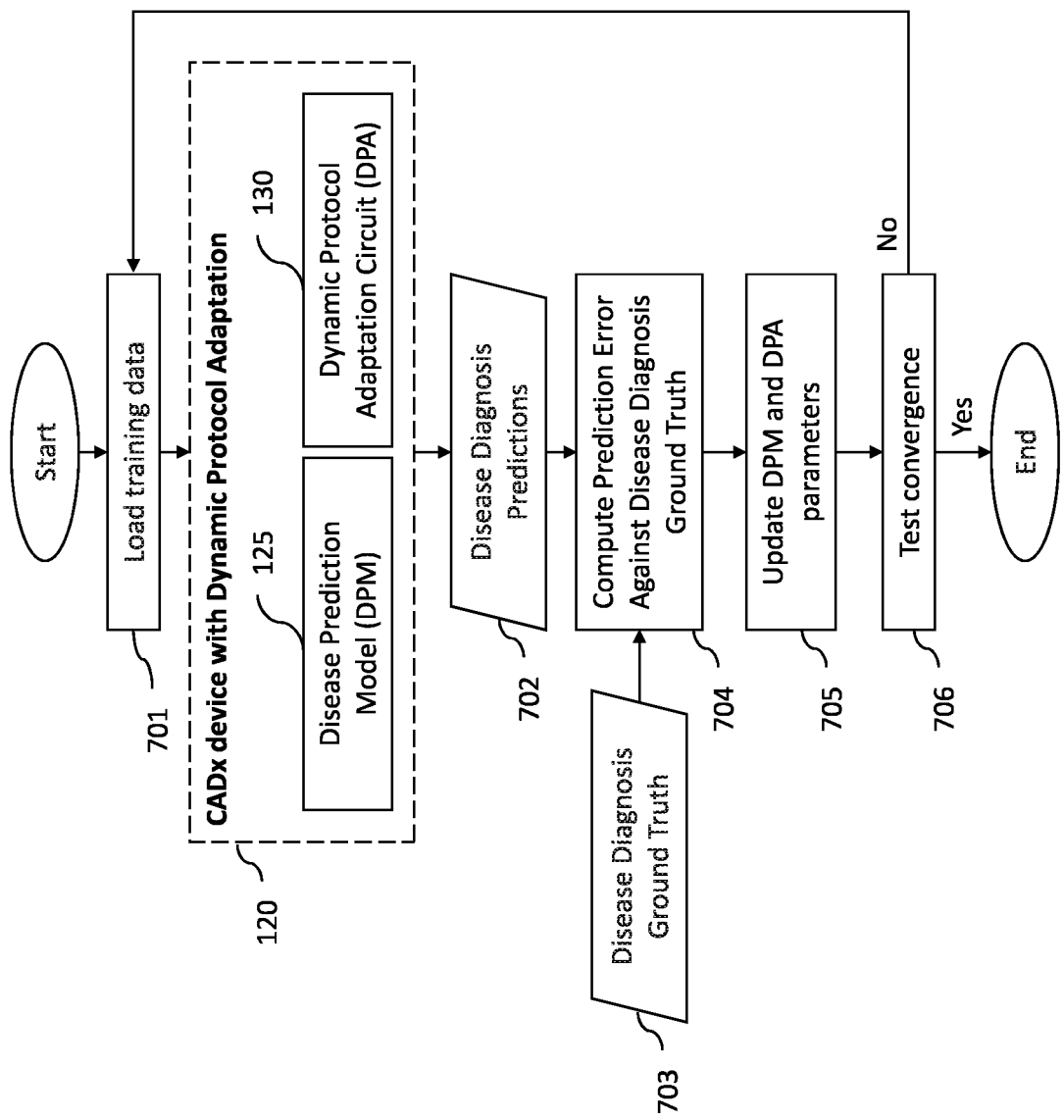
FIG. 4A shows an example of training process according to an embodiment of the invention.

In this example, FIG. 4A depicts an example of this training process. The first step is to load training input data (701), preferably comprised of both the medical input data (115) and one or more of the parameters (acquisition/reconstruction) that constitute the scan protocol information (116) for the input image in the input data. The approach to loading this data could follow standard practices of batching and data augmentation. This training data is then fed to the CADx device with dynamic protocol adaptation (120). In the previous process, for each case some of the training input data would go to the disease prediction model (125), such as any clinical parameters (112) and some to the dynamic protocol adaptation circuit (130) such as one or more parameters that make up the scan protocol information (116), and in some examples the same data could be input to both as well, such as the medical image(s) (111). The output of this step is a disease diagnosis prediction (702) which is compared against the disease diagnosis ground truth (703), which is the true diagnosis of the case as provided in the medical data and therefore the gold standard which a model with perfect predictive power should predict in the absence of diagnostic mistakes. This comparison is performed by computing a prediction error (704), usually in the form of a cost function or performance metric. This computed prediction error is then used to update the model parameters that parametrise the CADx device, both for the disease prediction model (125) and for the dynamic protocol adaptation circuit (130) in order to minimise the cost function with, for example, standard gradient-descent optimisation algorithms. These parameters are the previously introduced $\theta_{DPM}$ and $\theta_{DPA}$. To finalise an iteration, the algorithm tests for convergence (706) of one or multiple performance metrics or cost function appropriate for the task as is standard in machine learning model optimisation. If the training process has not converged, then the next iteration begins by loading the next batch of training data (701). In any iteration of this training process, if the convergence test (706) is satisfactory, the model training is deemed finished and so the optimisation procedure ends. A possible convergence test (706) could be that a monitored error metric over a "tuning" set of data does not decrease for several iterations. This "tuning" set of data would be separate from the training data and is sometimes also referred to as "validation set" or "development set".

Embodiment 2— Protocol is Used by DPA to Adjust DPM Through Parametrisation

In some other examples of the invention, the approach to protocol-based adaptation is be embodied through altering the disease prediction model (125) itself depending on the input scan protocol information (116).

Figure 3B:
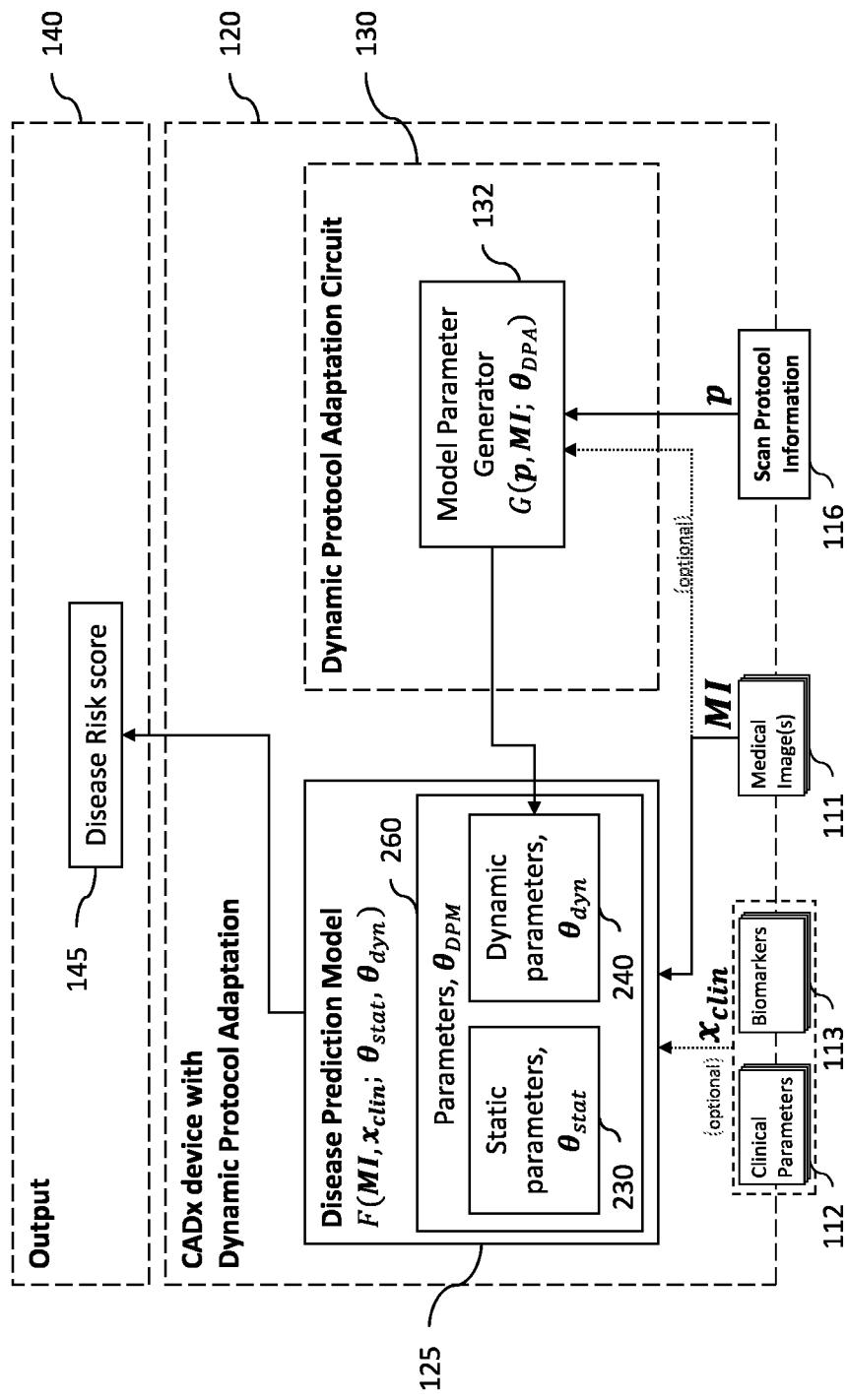
FIG. 3B shows an embodiment of the CADx system with a protocol-based adaptation circuit.

FIG. 3B shows the diagram of an example implementation of such a CADx device (120) with this type of dynamic protocol adaptation circuit (130). Central to the CADx device (120) is a machine learning model for disease prediction (125) that receives medical model input data such as the medical image(s) (111) and optionally one or more of the clinical parameters (112) and biomarkers (113). The disease prediction model (125) is parametrised by a set of parameters or coefficients $\theta_{DPM}$ (260). These parameters are those which define the mathematical operations through which the input data such as the medical image(s) go through. Each operation's result can be thought of as an intermediate representation of the medical input. Eventually, this representation is passed through a final operation and converted into a disease risk score. Preferably, the disease risk score will be a risk score for a lung disease. Therefore, the disease prediction model can be expressed as the following function $$\text{DiseaseRiskScore} = F(x; \theta_{DPM}) \qquad (2.1)$$

where x is the collection of medical input data (115).

Parallel to the machine learning model for disease prediction (125) is the dynamic protocol adaptation circuit (130) containing a model parameter generator (132). This generator, G, takes as input scan protocol information (116) such as one or more of the acquisition parameters (117), and/or reconstruction parameters (118) and/or derived features (119), and in some cases also the input medical image(s) (111) themselves, and generates a set of adjustments for the disease prediction model (125). In some examples of the invention, this set of adjustments to the disease prediction model (125) can take the form of a set of parameters that parametrise a subset or all of the mathematical operations of the disease prediction model (125). The disease prediction model (125) is parametrised by a set of parameters, $\theta_{DPM}$ (260), which in itself is comprised of a subset of static parameters, $\theta_{stat}$ (230) and a set of dynamic parameters, $\theta_{dyn}$ (240), as $\theta_{DPM} = \theta_{stat} \oplus \theta_{dyn}$, where $\oplus$ is the concatenation operator. The static parameters $\theta_{stat}$ are those which do not depend on the scan protocol of the input image, and the dynamic parameters $\theta_{dyn}$, which partly or fully parametrise the disease prediction model (125), F, are the output of the model parameter generator (132) and are therefore dependent on the scan protocol information.

$$\theta_{dyn} = G(p, \text{MI}; \theta_{DPA}) \qquad (2.2)$$

where G is the model parameter generator and p is the set of scan protocol information input (116) and MI are the medical image(s) (111).

Therefore, the set of operations of F and consequently, the inner feature representations for a specific image become dependent on its scan protocol information, p, as follows:

$$\text{DiseaseRiskScore} = F(\text{MI}, x_{clin}; \theta_{stat}, \theta_{dyn}(p)) \qquad (2.3)$$

where $x_{clin}$ is the collection of any clinical parameters (112) and/or biomarkers (113), and p is the scan protocol information (116).

Note that in this example, the disease prediction model F (125) does not take the scan protocol information as input, rather it is partly or fully parametrised with scan protocol-dependent parameters $\theta_{dyn}$ (240).

In some examples of the invention, the model parameter generator G (132) is another machine learning model.

In some examples of this invention, the dynamic protocol adaptation circuit (130) may take other inputs which may have scan protocol information embedded in them. An example could be to directly take in the medical scan image(s) itself (111), as can be seen in FIG. 2A and FIG. 3B for Embodiment 2. The medical scan image is, in part, the result of all the scan protocol parameters used to obtain the scan image and therefore can be a useful derived representation of the protocol parameters. Additionally, this representation may capture some scan protocol-specific characteristics that may not be directly available from just using the scan protocol parameters.

In some examples of the invention, the disease prediction model (125) and the dynamic protocol adaptation circuit (130) can both be part of the same trainable machine learning model as, for example, a pair of combined neural networks and/or convolutional neural networks which can be trained end-to-end. This would allow for simultaneous training of both the disease prediction model (125) and the dynamic protocol adaptation circuit (130).

In this example of the invention, the training process is as previously described with respect to FIG. 4A depicts an example of a training process. The first step is to load training input data (701) comprised of both the medical input data (115) and the scan protocol information (116), as previously described.

In this embodiment of the invention where disease model prediction (125) is parametrised through a model parameter generator (132) within the dynamic protocol adaptation circuit (130), an extra step occurs within the CADx device (120) which involves substituting the relevant model parameters of the disease prediction model (125) with those generated by the dynamic protocol adaptation circuit (130). In some examples of the invention, this could involve predicting and substituting the convolutional filters in the first few convolutional layers of the disease prediction model (125). In such a scenario, standard gradient-descent optimisation algorithms would still applicable.

Embodiment 3— Protocol is Used by DPA to Adapt Medical Image(s) Before Inputting to DPM In some other examples of the invention, the approach of protocol-based adaptation is embodied through generating an alternative protocol-dependent representation of the medical scan image(s) before inputting these alternative scan protocol adapted images (134) into the disease prediction model (125).

Figure 3C:
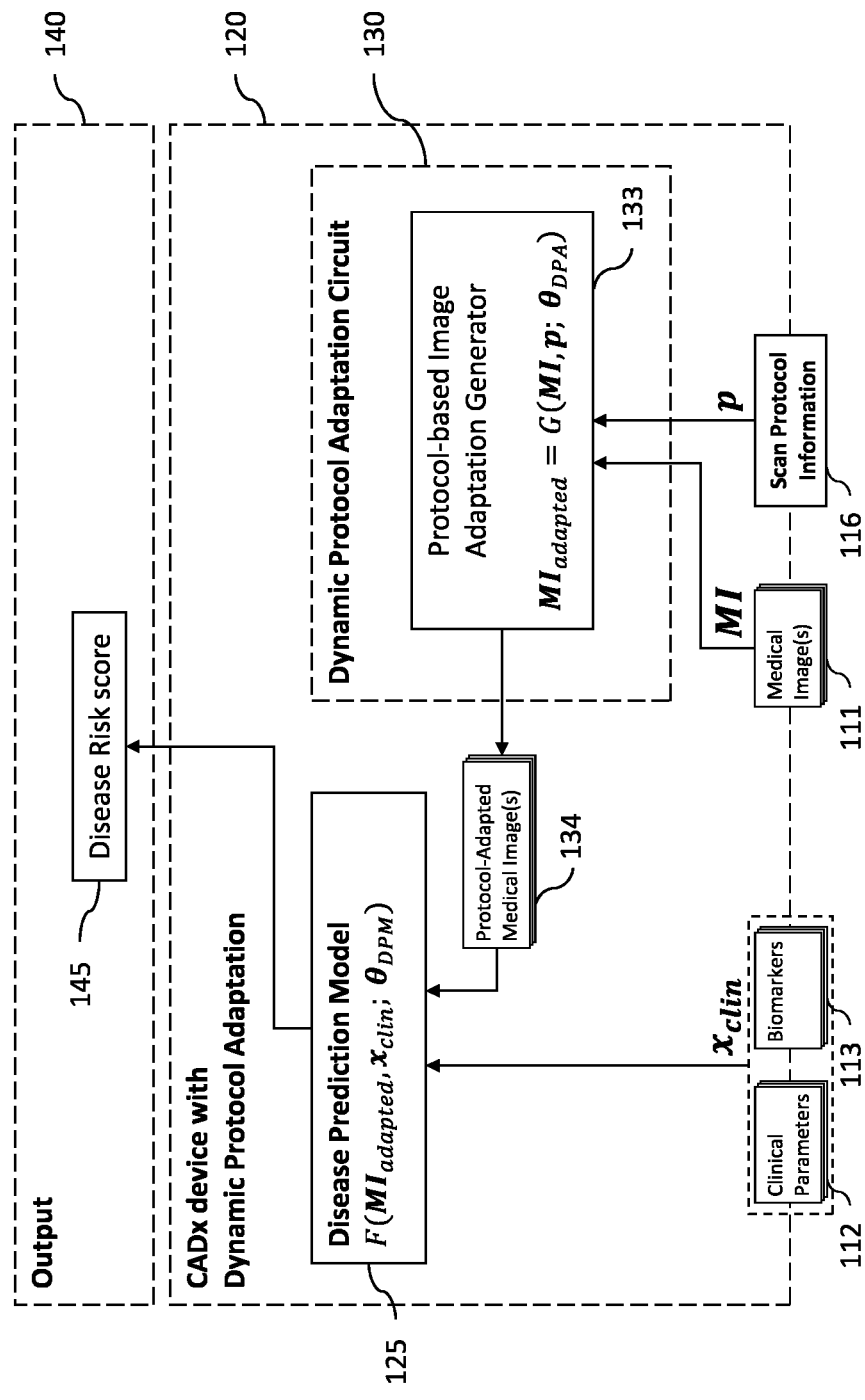
FIG. 3C shows an alternative embodiment of the CADx system with a protocol based adaptation circuit.

FIG. 3C shows the diagram of an example implementation such a CADx device (120) with this type of dynamic protocol adaptation. Central to the CADx device (120) is the machine-learning based disease prediction model (125). In this example of the invention, the one or more inputs to the disease prediction model (125) are a scan protocol-adapted representation of the medical image(s) (134) as well as one or more of the clinical parameters (112) and biomarkers (113). The dynamic protocol adaptation circuit (130) is comprised of a protocol-based image adaptation generator (133), G, which takes in the original input medical image(s), MI (111) and scan protocol information, p (116), and generates a transformed version of the medical image(s) (134) informed by the image(s) acquisition and reconstruction protocol as $$MI_{adapted} = G(MI, p; \theta_{DPA}) \quad (3.1)$$

where $\theta_{DPA}$ are the protocol-based image adaptation generator's model parameters and $MI_{adapted}$ is the protocol-adapted medical image (134). This protocol-adapted medical image (134) may conserve the spatial dimensionality and number channels of the original image for example the original image may be a CT scan patch of 20 slices of 200 by 200 pixels, resulting in a volume of 20×200×200 voxels. In some examples of this invention, the adapted medical image may be a lower-dimensional representation, such as for example, and following the previous example, reducing the dimensionality in the slice direction resulting in an adapted medical image with e.g., 5 channels or adapted slices and 5×200×200 voxels. It is generally the case that the intrinsic structure of many high-dimensional data, such as images, is condensed in a lower-dimensional space or "manifold" within the high-dimensional space. Lowering the dimensionality of the adapted medical image could have the benefit of reducing or distilling the complexity of the input visual representation to its most informative components in much a similar manner as autoencoder networks do, while also decreasing the computational cost in terms of memory and speed. In some examples of this invention, the adapted medical image that will be input to the CADx device may be a higher-dimensional representation of the original image as increasing dimensionality may allow for more representational power by increasing the possible number of derived features to be computed from the original medical image.

In this embodiment of the invention, the disease prediction model (125) does not take in the original medical image(s) (111) directly, but the output disease risk score (145) becomes dependent on the original image(s) (111) and the scan protocol information (116) via the protocol-adapted image (134), which combines the original medical image (111) and the scan protocol information 116. The disease risk score (145) for this embodiment of the invention can therefore be expressed as $$DiseaseRiskScore = F(MI_{adapted}(MI, p), x_{clin}; \theta_{DPM}) \quad (3.2)$$

where $x_{clin}$ is the collection of one or more of the clinical parameters (112) and/or biomarkers (113).

In some examples of the invention, the disease prediction model (125) and the dynamic protocol adaptation circuit (130) can both be part of the same trainable machine learning model as, for example, a pair of combined neural networks and/or convolutional neural networks which can be trained end-to-end. This would allow for simultaneous training of both the disease prediction model (125) and the dynamic protocol adaptation circuit (130). In this context, training means to find the values of the parameters of a machine learning model which minimise a particular error metric over a training set of data through computational optimisation. The training for this embodiment is as previously described with respect to FIG. 4A.

Addressing Missing Scan Protocol Information

In an embodiment of this invention, the CADx device (120) incorporates the ability to adapt to the medical image(s) scan protocol information (116). In some cases, it is expected that part or all of the scan protocol information (116) may be missing. It would therefore be advantageous to incorporate the ability to handle such scenario, where the scan protocol information is incomplete.

Figure 4B:
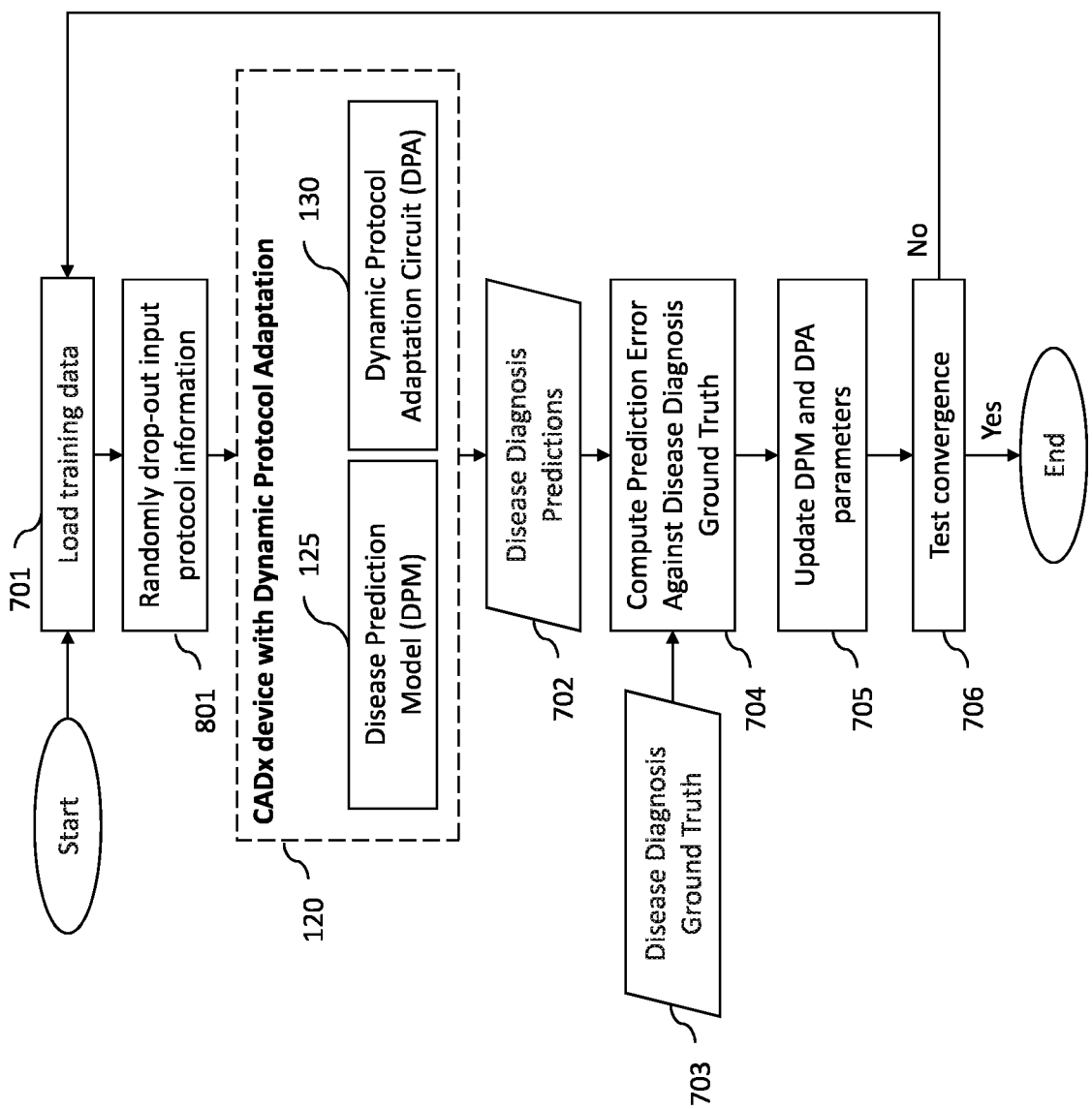
FIG. 4B shows an alternative embodiment of the training process for this invention.

In some examples of this invention, this could be achieved through a modification of the CADx model training method without further modification of the arrangement of the CADx device (120). In FIG. 4B a modification to the training method of FIG. 4A is depicted, where a stochastic drop-out step (801) is applied to the input training data, prior to the training data being provided to the CADx device between step 701 and 702. In this intermediate step 801, the aim is to augment the training data loaded in step 701 in order to make the CADx device (120) able to handle the case in which specific scan protocol parameters are missing. In some examples, the scan protocol information (116) may be input through a set of continuous or discrete encodings, such as a one-hot encoding for each protocol parameter. Then, a specific point in that encoding space such as for example, the zero vector, may be chosen to represent a missing scan protocol parameter. During training, the stochastic drop-out step (801) sets protocol parameters as missing according to some policy, preferably by a random process with a predetermined probability for each scan protocol parameter. When a scan protocol parameter is removed, it is simply substituted by the zero-vector. Note that outside of training, at the time of making predictions, this stochastic drop-out step is not applied and instead, the model is able to handle missing parameters by converting the missing parameter(s) to the zero-vector.

Addressing Inadequate Protocol Information

Apart from missing scan protocol information, there may be scan protocol parameters input into the disease prediction model which may not be adequate either through human error or through not being well-represented in the training data.

Figure 5:
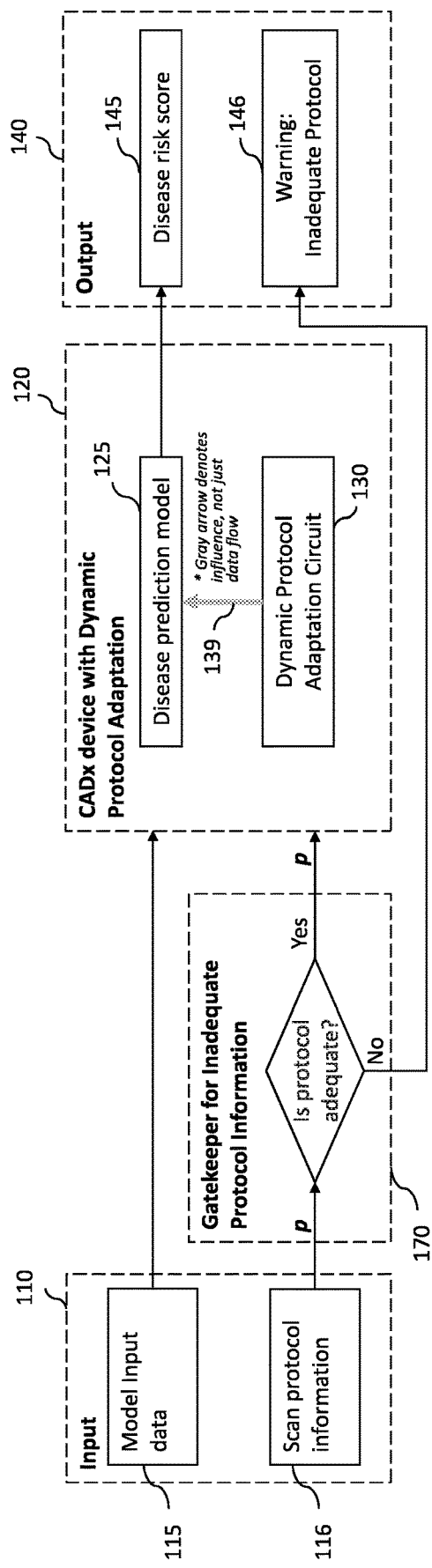
FIG. 5 shows an embodiment of a CADx system with a protocol gatekeeper.

FIG. 5 shows an altered high-level schematic of a CADx device (120) which can handle inadequate scan protocol information. In some examples of this invention, a Gatekeeper for Inadequate Protocol Information (170) circuit validates the scan protocol information (116) before it is provided to the dynamic protocol adaptation circuit (130), this validation is done against a predefined set of accepted values for the scan protocol information and issues a warning (146) when the scan protocol information is not acceptable when compared to the predefined set of values, bypassing the CADx device (120). These ranges of accepted values for the scan protocol information may be defined in a single-parameter basis or in a multi-variate manner i.e. ranges which define what combinations of scan protocol parameters are accepted. In another example of the invention, the Gatekeeper for Inadequate Protocol Information (170) evaluates the likelihood of the received scan protocol information (116) being acceptable for the CADx system, where the evaluation is based on a statistical model built from the training data and issues a warning if the likelihood of the scan protocol information (116) is below a threshold $TH_{likelihood}$. $TH_{likelihood}$ is preferably defined empirically to balance the frequency with which warnings (146) are issued and prediction is bypassed. In some examples of this invention, the statistical model used for this evaluation is a mixture of Gaussians, which is fitted to the received scan protocol information of the training data using the well-known expectation maximisation algorithm. In some embodiments of the invention the warning may also include a warning that the disease risk score is not reliable.

Multi Time Point Input

In some examples of this invention, the CADx system (120) supports the input of multiple medical scan images corresponding to multiple time points of the same anatomical structure in order to assess temporal evolution of, for example, a lesion. These multiple medical scan images, while relating to the same anatomical structure, may be acquired through different scan acquisition and/or reconstruction protocols. Of course, in an alternative embodiment of the invention, they may be acquired with the same acquisition and reconstruction parameters.

In these examples, the model input data (115) is comprised of this history of multiple medical scan images (111) and the scan protocol information (116) is comprised of multiple sets of protocol parameter information corresponding to each of the medical scan images. The use of a CADx device (120) with scan protocol adaptation, as it relates to this invention, would therefore be beneficial for such a multi time point scenario.

In the various embodiments of the invention as described, the CADx device (120) is deployed to receive and analyse medical images obtained under a variety of different scan acquisition and reconstruction protocols. These variations in scan acquisition and reconstruction protocols can affect the prediction ability of standard CADx devices. The common practice is for machine learning based CADx device manufacturers to train static CADx devices on large datasets which contain a rich enough distribution of scan protocols so as to bring the final CADx device to a certain degree of protocol-invariance. However, in practice, this invariance is both usually not achieved nor necessarily desirable. On the latter point, inducing protocol-invariance may affect the overall performance of the CADx device by reducing its ability to exploit protocol-dependent characteristics of the medical image(s). The CADx device of this invention implements a dynamic protocol adaptation circuit (130) which addresses this problem by leveraging various modes of scan protocol information corresponding to the image being processed and dynamically generating a set of protocol-dependent adjustments or inputs to the disease prediction model as used in the CADx device. Therefore, this invention aims to make the CADx device both more performant and robust to real-world to the protocol variability of medical image(s).

This invention can be applied in any context where a CADx device, powered by a machine learning model, and a method for analysing scan images using a CADx device are used to assess the risk of disease from input medical data such as medical images, to provide a disease risk score and where the instantiation of this medical input data can vary according to available scan acquisition and reconstruction parameters.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for receiving at least one input medical image of a patient in which the patient's lungs are visible.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media e.g., CD ROM, CD R, etc. and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing running program or portion of a program, current program values and state information, and the resources used by the operating system to manage the execution of the process. An operating system OS is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output I/O devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A computer aided diagnosis CADx system for analysing medical scan images generated using an imaging modality and determining a disease risk score for the medical scan image comprising:
    a processor comprising an input circuit for receiving an input comprising at least one medical scan image;
    a dynamic protocol adaptation circuit for receiving and analysing scan protocol information, wherein the scan protocol information comprises at least one of: one or more acquisition parameters, one or more reconstruction parameters, one or more features resulting from the combination of acquisition and reconstruction parameters, for the at least one medical scan image and providing a dynamic output from the protocol adaptation circuit as an input to a disease prediction model based on the received scan protocol information; wherein at least one of the disease prediction model and the dynamic protocol adaptation circuit consist of a machine learning model, trained using training data comprising medical input data, wherein the medical input data comprises at least one of: one or more of medical scan images, one or more clinical parameters, one or more biomarkers and ground truth labels associated with the medical input data and scan protocol information; wherein the training data is provided to the disease prediction model and the dynamic protocol adaptation circuit so that the disease prediction model and dynamic protocol adaptation circuit are trained to recognise input medical scan images and scan protocol information, wherein during the training with the machine learning model, one or more of the scan protocol parameters from the training data is dropped out before the training data is provided to the disease prediction model and/or the dynamic protocol adaptation circuit, the dropped scan protocol parameters are replaced with a missing protocol parameter value, and training is performed with the reduced training set and the missing protocol parameter value, and the disease prediction model and/or dynamic protocol adaptation circuit are trained to handle input medical scan images that have missing scan protocol information; wherein, when the CADx system encounters an input medical scan image with missing scan protocol information, the CADx system will substitute the missing protocol information with the missing protocol parameter value so the input medical scan image can be analysed for a disease risk score and
    said processor comprising an output circuit to produce an output that is the disease risk score calculated from the disease prediction model for the at least one medical scan image.

2. A CADx system as claimed in claim 1, wherein the scan acquisition parameters comprise one of more of: details of a scan contrast agent; tube voltage for the image acquisition;

tube current for the image acquisition; beam filter type; scanning mode; field of view and slice spacing and the scan reconstruction parameters comprise one or more of: reconstruction algorithm, slice thickness and convolutional kernel.

3. A CADx system as claimed in claim 1, wherein the derived scan protocol features comprise one or more of noise level and image sharpness, as derived from the input medical scan image.

4. A CADx system as claimed in claim 1, wherein the output of the dynamic protocol adaptation circuit provided as an input to the disease prediction model is either a data input, or an adjustment or modification to the disease prediction model.

5. A CADx system as claimed in claim 1, wherein the at least one medical scan image input to the input circuit is also provided to at least one of the dynamic protocol adaptation circuit and the disease prediction model.

6. A CADx system as claimed in claim 1, wherein the input circuit receives multiple input scan images over a period of time to assess changes in structures shown in the images.

7. A CADx system as claimed in claim 1, wherein the disease prediction model includes one or more static parameters that are independent of the scan protocol for the input image and one or more dynamic parameters, wherein an adjustment or modification to the disease prediction model resulting from the output of the dynamic protocol adaptation circuit, affects the dynamic parameters in the disease prediction model, while the static parameters remain unchanged.

8. A CADx system according to claim 1, wherein the output further comprises a warning that the scan protocol information for the input medical scan image is inadequate, and the disease risk score may not be reliable.

9. A CADx system according to claim 8, further comprising a protocol gatekeeper circuit that receives the scan protocol information before it is provided to the dynamic protocol adaptation circuit and determines if the scan protocol information is inadequate.

10. A CADx system according to claim 1, wherein the input medical scan image is one of: a CT image, an MRI image, a PET image, an X-ray image, an ultrasound image or a SPECT image.

11. A CADx system according to claim 1, wherein the input further comprises one or more of: biomarkers for the patient or clinical parameters for the patient wherein the biomarkers and clinical parameters comprise at least one of: patient age, patient sex, family and clinical history, results of blood tests, results of lung function tests.

12. A method for analysing medical scan images generated from an imaging modality and determining a disease risk score for the medical scan image: the method comprises the following step:
receiving at least one input medical scan image;
analysing scan protocol information with a dynamic protocol adaptation circuit providing an input to a disease prediction model based on the analysed scan protocol information, wherein the scan protocol information comprises at least one of: one or more acquisition parameters, one or more reconstruction parameters, one or more features resulting from the combination of acquisition and reconstruction parameters; wherein at least one of the disease prediction model and the dynamic protocol adaptation circuit consist of a machine learning model, trained using training data comprising medical input data, wherein the medical input data comprises at least one of: one or more of medical scan images, one or more clinical parameters, one or more biomarkers and ground truth labels associated with the medical input data and scan protocol information; wherein the training data is provided to the disease prediction model and the dynamic protocol adaptation circuit so that the disease prediction model and dynamic protocol adaptation circuit are trained to recognise input images and scan protocol information, wherein during the training with the machine learning model, one or more of the scan protocol parameters from the training data is dropped out before the training data is provided to the disease prediction model and/or the dynamic protocol adaptation circuit, the dropped scan protocol parameters are replaced with a missing protocol parameter value, and training is performed with the reduced training set and the missing protocol parameter value, and the disease prediction model and/or dynamic protocol adaptation circuit are trained to handle input images that have missing scan protocol information; wherein, when the CADx system encounters an input image with missing scan protocol information, the CADx system will substitute the missing protocol information with the missing protocol parameter value so the input image can be analysed for a disease risk score; and
producing an output that is the disease risk score calculated from the disease prediction model for the at least one medical scan image.

13. A method as claimed in claim 12, wherein the step of providing an output from the dynamic protocol adaptation circuit as an input to a disease prediction model comprises further comprising the step of:
providing the input as either a data input, or an adjustment or modification to the disease prediction model.

14. A method as claimed in claim 12, wherein the scan acquisition parameters comprise one of more of: details of a scan contrast agent; tube voltage for the image acquisition; tube current for the image acquisition; beam filter type; scanning mode; field of view and slice spacing, and the scan reconstruction parameters comprise one or more of: reconstruction algorithm, slice thickness and convolutional kernel, and the derived scan protocol features comprise spatial resolution, noise level and image sharpness as derived from the medical scan image(s).

* * * * *